United States Patent [19]

Kübler et al.

[11] Patent Number: 5,198,553

[45] Date of Patent: Mar. 30, 1993

[54] PROCESS FOR THE PRODUCTION OF GRAMINE DERIVATIVES

[75] Inventors: Wolfgang Kübler; Gregor Haffer; Reiner Wierzchowski; Klaus Nickisch, all of Berlin, Fed. Rep. of Germany

[73] Assignee: Schering Aktiengesellschaft, Berlin and Bergkamen, Fed. Rep. of Germany

[21] Appl. No.: 778,878

[22] PCT Filed: Apr. 23, 1991

[86] PCT No.: PCT/DE91/00353

§ 371 Date: Dec. 26, 1991

§ 102(e) Date: Dec. 26, 1991

[87] PCT Pub. No.: WO91/16304

PCT Pub. Date: Oct. 31, 1991

[30] Foreign Application Priority Data

Apr. 26, 1990 [DE] Fed. Rep. of Germany ....... 4013907

[51] Int. Cl.⁵ .......................................... C07D 209/14
[52] U.S. Cl. .................................... 548/504; 548/507
[58] Field of Search ....................... 548/504, 507, 516

[56] References Cited

U.S. PATENT DOCUMENTS 3,459,767 8/1969 McManus et al. .................. 548/504

FOREIGN PATENT DOCUMENTS 0054507 6/1982 European Pat. Off. ............ 548/504

OTHER PUBLICATIONS

Raines, et al., A Study on the Condensation of Pyrroles, J. of Het. Chem., vol. 7, No. 1, pp. 223–225, Feb. 1970.

Primary Examiner—Robert W. Ramsuer
Attorney, Agent, or Firm—Millen, White, Zelano and Branigan

[57] ABSTRACT

A process for the production of gramine derivatives is described, which is characterized in that an indole is reacted with an imine under acid catalysis in the presence of primary amines.

6 Claims, No Drawings

PROCESS FOR THE PRODUCTION OF GRAMINE DERIVATIVES

The invention relates to a process for the production of gramine derivatives.

Gramines are intermediate products for the synthesis of pharmacologically applicable compounds, such as, for example, for the production of tryptamines (C.A. 56, 11701 (1962), tryptophans, (R. V. Heinzelmann et al., Org. Chemie [Chemistry] 25, 1548 (1960)) and carbolines (EP-A-239667).

Because of their good binding affinity to the benzodiazepine receptors, β-carbolines show effects on the central nervous system and therefore have just recently met with great interest in the research of pharmaceutical agents. While gramine formation with formaldehyde and secondary amines often occurs problem-free, the reaction of indole with aldehydes and primary amines is possible only with poor yields (H. R. Snyder et al., J. Am. Soc. 79. 2217 (1957)). With the use of the corresponding imines, the yield is actually better, but still always unsatisfactory as a function of the substituents of the indole.

Therefore, the object was to develop a process which, because of its good yields with simultaneously good handling and without expensive separation operations, makes possible the production on an industrial scale of these β-carboline intermediate stages.

Surprisingly, it has now been found that the reaction of indole derivatives with imines occurs with almost quantitative yields, if the primary amines corresponding to the imine are added to the reaction mixture.

Since neither an additional reaction step is required by the addition of amine nor do by-products that are difficult to separate result, this process is very well-suited for the synthesis on an industrial scale of this important intermediate compound for the production of valuable pharmaceutical agents.

The invention relates to the process for the production of compounds of formula I

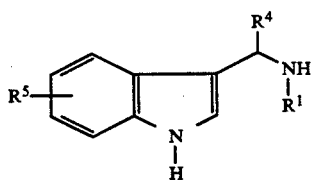

in which
$R^1$ is $C_{1-4}$ alkyl,
$R^4$ is $C_{1-4}$ alkyl or $C_{1-4}$ alkoxy-$C_{1-2}$ alkyl,
$R^5$ is $OR^6$ or $CHR^7R^8$, and
$R^6$ is $C_{1-4}$alkyl, $C_{3-6}$cycloalkyl or an optionally substituted aralkyl radical,
$R^7$ is hydrogen or $C_{1-4}$ alkyl,
$R^8$ is hydrogen, $C_{1-4}$ alkyl, $OR^9$ or $NR^{10}R^{11}$ with $R^9$ meaning $C_{1-4}$ alkyl and $R^{10}$ and $R^{11}$ are the same or different and mean hydrogen, $C_{1-4}$alkyl or together with the nitrogen atom mean an optionally saturated heterocyclic 5- or 6-ring containing another heteroatom, which is optionally substituted with one to two $C_{1-4}$ alkyl groups, characterized in that an indole derivative derivative of formula II

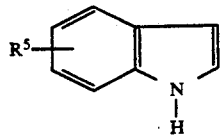

in which $R^5$ has the above-named meaning is reacted with an imine of formula III $$R^4-CH=N-R^1 \qquad \text{III,}$$

in which
$R^4$ and $R^1$ have the above-named meaning, under acid catalysis in the presence of primary amines.

Substituent $R^5$ can be in 4-, 5-, 6- and/or 7-position once or twice, and the substitution is preferably in 4- or 5-position.

$C_{1-4}$alkyl is to be understood to mean respectively a straight or branched alkyl group with 1-4 carbon atoms, such as, for example, methyl, ethyl, propyl, isopropyl, butyl, sec-butyl, tert-butyl and isobutyl.

Suitable cycloalkyl radicals are, for example, cyclopropyl, cyclobutyl, cyclopentyl and cyclohexyl.

If $R^{10}$ and $R^{11}$ together with the nitrogen atom mean a 5- or 6-membered heterocycle optionally containing another heteroatom, such as oxygen, nitrogen or sulfur, this heterocycle represents, for example, morpholine, piperidine, thiomorpholine, piperazine or pyrrolidine and can optionally be substituted with one to two $C_{1-4}$alkyl groups, such as, for example, 2,6-dimethylmorpholine and N-methylpiperazine.

Aralkyl radical $R^6$ can contain 7-8 carbon atoms and preferably represents the phenyl-$C_{1-2}$alkyl radical, such as, for example, benzyl, phenethyl and α-methylbenzyl.

As substituents of the aralkyl radical, halogens, such as fluorine, chlorine, bromine or iodine, $C_{1-4}$alkoxy or $C_{1-4}$ alkyl are suitable, and the substituent can be in each position of the aryl radical once or twice. As a preferred aralkyl radical, the benzyl radical, which can be substituted with halogen once or twice, such as 3-bromobenzyl and 4-chlorobenzyl, can be considered.

As a preferred substituent combination for the process according to the invention, $R^4$ meaning $C_{1-4}$alkoxy-$C_{1-2}$alkyl and $R^5$ meaning $OR^6$, with $R^6$ in the above-mentioned meaning, can be considered.

The reaction according to the invention is performed acid-catalyzed, for example, with organic acids, such as formic acid, acetic acid, propionic acid or mixtures of organic acids. The primary amine added to the reaction mixture advantageously corresponds to amine $R^1$-$NH_2$ used for imine production to simplify the working up of the reaction. Of course, other aliphatic amines are also suitable.

As solvent, inert solvents such as hydrocarbons, chlorinated hydrocarbons or cyclic or acyclic ethers, such as, for example, toluene, benzene, xylene, diethyl ether, dimethoxymethane or methyl-tert-butylether can be added or the reaction is performed in suspension.

The process is performed generally at temperatures of −20° C. up to room temperature. The imine is added in equivalent amounts or in excess.

After about 0.5 to 24 hours, the reaction is completed. It is worked up in the usual way and the end product is isolated by filtration and crystallization. The thus obtained compounds of formula I can be converted to pharmaceutical agents with very good effectiveness according to the process described, for example, in EP-54507 and EP-A-239667.

The production of the initial compounds is known or takes place according to known processes.

The following examples are to explain the process according to the invention.

Production of the Initial Compound 72.5 ml of isopropylamine is dissolved in 115 ml of toluene under nitrogen atmosphere and mixed at 0° C. with 56.5 ml of methoxyacetaldehyde. After 30 minutes, 38 g of potassium carbonate is added and then filtered. The residue is washed with toluene. The volume of the solution is about 400 ml. The imine produced without toluene shows the following $^1$H-NMR spectrum: 90 MHz (CDCl$_3$):

7.74 tr J=4Hz (1); 4.04 d J=4 Hz (2); 3.70 s (3); 3.69 m (1); 1.18 d J=6 Hz (6)

EXAMPLE 1

Production of the 5-Benzyloxygramine Derivative 340 ml (1.6 equivalent) of imine solution is instilled in a suspension of 95 g of 5-benzyloxyindole, 300 ml of toluene, 300 ml of glacial acetic acid, 200 ml of formic acid and 100 ml of isopropylamine at −10° C. It is allowed to stir for one hour, and the reaction mixture is added to 800 ml of water. The aqueous phase is extracted twice with toluene and then adjusted from pH 3 to pH 11.5–12.0 with 50% sodium hydroxide solution and potassium carbonate. The resulting precipitate is filtered off, washed with water and dried.

Yield: 137 g of 5-benzyloxypseudogramine=95.2% of theory.

Melting point: 109°–111° C.

EXAMPLE 2

Production of the 4-Benzyloxygramine Derivative 53.2 ml (2.5 equivalents) of the imine solution is instilled in a solution of 9.4 g of 4-benzyloxyindole, 10 ml of toluene, 30 ml of glacial acetic acid, 20 ml of formic acid and 10 ml of isopropylamine at −10° C. It is allowed to stir for three hours and the reaction mixture is added to 300 ml of water. The aqueous phase is extracted twice with toluene and then adjusted from pH 3 to pH 11.5–12.0 with 50% sodium hydroxide solution and potassium carbonate. The resulting precipitate is filtered off, washed with water and dried.

Yield: 12.87 g of 4-benzyloxypseudogramine=90.4% of theory.

Melting point: 127°–133° C.

We claim:

1. A process for the production of a compound of formula I

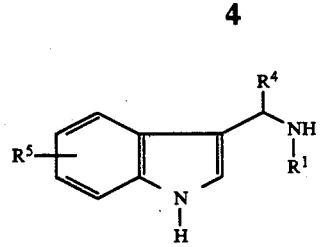

wherein
$R^1$ is $C_{1-4}$ alkyl;
$R^4$ is $C_{1-4}$ alkyl or $C_{1-4}$ alkoxy-$C_{1-2}$ alkyl;
$R^5$ is $OR^6$ or $CHR^7R^8$;
$R^6$ is $C_{1-4}$ alkyl, $C_{3-6}$ cycloalkyl or a hydrocarbon $C_{7-8}$ aralkyl group which is optionally mono- or di-substituted with a halogen, a $C_{1-4}$ alkoxy group, or a $C_{1-4}$ alkyl group;
$R^7$ is hydrogen or $C_{1-4}$ alkyl;
$R^8$ is hydrogen, $C_{1-4}$ alkyl, $OR^9$ or $NR^{10}R^{11}$ with $R^9$ meaning $C_{1-4}$ alkyl and $R^{10}$ and $R^{11}$ are the same or different and mean hydrogen, $C_{1-4}$ alkyl or together with the nitrogen atom means an optionally saturated heterocyclic 5- or 6-ring containing a heteroatom which is oxygen, nitrogen or sulfur, which is optionally substituted with one to two $C_{1-4}$ alkyl groups, comprising reacting an indole derivative of formula II

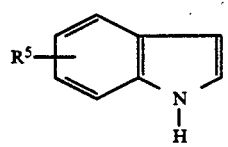

wherein $R^5$ has the above-named meaning, with an imine of formula III

$$R^4-CH=N-R^1 \qquad III,$$

wherein
$R^4$ and $R^1$ have the above-named meanings, under acidic catalysis conditions in the presence of an effective amount of a primary amine.

2. The process according to claim 1, wherein $R^1$ is isopropyl.

3. The process of claim 1, wherein the heterocyclic 5- or 6-ring is morpholine, piperidine, thiomorpholine, piperazine, pyrrolidine, 2,6-dimethylmorpholine or N-methylpiperazine.

4. The process of claim 1, wherein the primary amine corresponds to the amine $R^1$-$NH_2$ used for the imine production.

5. The process of claim 1, wherein the catalytic conditions are accomplished using an organic acid.

6. The process of claim 1, wherein the compound of formula I is 5-benzyloxypseudogramine or 4-benzyloxypseudogramine.

* * * * *